United States Patent
Shuch et al.

(12)

(10) Patent No.: US 6,503,483 B2
(45) Date of Patent: *Jan. 7, 2003

(54) DENTAL FORMULATION

(75) Inventors: David J. Shuch, Lafayette, NJ (US); Gerald P. Curatola, East Hampton, NY (US)

(73) Assignee: C.S. Bioscience, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/818,807

(22) Filed: Mar. 27, 2001

(65) Prior Publication Data

US 2002/0054857 A1 May 9, 2002

Related U.S. Application Data

(63) Continuation-in-part of application No. 09/209,621, filed on Dec. 11, 1998, now Pat. No. 6,207,137, which is a continuation-in-part of application No. 08/874,107, filed on Jun. 12, 1997, now Pat. No. 5,925,335.

(51) Int. Cl.$^7$ .............................. A61K 7/16; A61K 7/26; A61K 35/78
(52) U.S. Cl. .......................... 424/49; 424/58; 424/195.1
(58) Field of Search ...................................... 424/49–58

(56) References Cited

U.S. PATENT DOCUMENTS

| | | | | | |
|---|---|---|---|---|---|
| 3,534,137 | A | * | 10/1970 | Matsumura et al. | 424/94 |
| 4,654,373 | A | * | 3/1987 | Bertelli | 514/690 |
| 5,378,461 | A | * | 1/1995 | Neigut | 424/94.1 |
| 5,401,502 | A | * | 3/1995 | Wundoruch et al. | 424/195.1 |
| 5,925,335 | A | * | 7/1999 | Shuch et al. | 424/49 |
| 6,207,137 | B1 | * | 3/2001 | Shuch et al. | 424/49 |

FOREIGN PATENT DOCUMENTS

| | | | |
|---|---|---|---|
| DE | 3124970 | * | 1/1983 |
| EP | 205 133 | * | 6/1985 |
| WO | 86 04503 | * | 8/1986 |
| WO | 94 06418 | * | 3/1994 |
| WO | 94 15595 | * | 7/1994 |
| WO | 98 56336 | * | 12/1998 |

* cited by examiner

*Primary Examiner*—Shep K. Rose
(74) *Attorney, Agent, or Firm*—Katten Muchin Zavis Rosenman

(57) ABSTRACT

An orally absorbable improved dental formulation is provided. The dental formulation includes a base to which an active component is added. The active component comprises, based on the overall weight thereof, Vitamin C in an amount between about 0 and 25 weight percent, and Co-enzyme Q-10 (or ubiquinone), in an amount between 0 and 25 weight percent, are added.

40 Claims, No Drawings

DENTAL FORMULATION

This application is a continuation-in-part of U.S. application Ser. No. 09/209,621, filed Dec. 11, 1998, now U.S. Pat. No. 6,207,137 which was a continuation-in-part of U.S. application Ser. No. 08/874,107 filed Jun. 12, 1997, now U.S. Pat. No. 5,925,335 and directed to DENTAL FORMULATION.

BACKGROUND OF THE INVENTION

Oral hygiene products have been in use for centuries. The most common of these products, toothpaste, typically consists of a mild abrasive dispersed in a gel or paste base, with detergents added to aid in cleaning, and fluoride added to reduce tooth decay. Nutritional supplements have been in use for less than a century and typically are supplied in forms to be swallowed and digested for subsequent dispersal throughout the body. Over the past one hundred and fifty years certain medications have been formulated to be absorbed directly through the mucus membranes of the mouth. Building on the evidence of high absorbability of medications through the lining of the mouth, nutritional supplements are also now recognized to be able to be absorbed in this way. Further, homeopathic remedies have, since their inception, been routinely administered via this route.

Although oral hygiene products presently on the market adequately address the need for cleaning the teeth and administering fluoride, no existing product takes full advantage of the ability of such a product to deliver to the oral cavity such nutrients and homeopathic remedies as would most benefit those individuals suffering from gum disease and tooth decay. It is well recognized that certain nutritional supplements are essential in reducing host susceptibility to chronic disease in the mouth.

Accordingly it would be desirable to provide a particular formulation of nutrients, including not only the more commonly used vitamins and minerals, but also including beneficial herbal ingredients as well as homeopathics, that act together to reduce and prevent major chronic diseases of the mouth.

Secondly, it would be desirable to provide such a formulation in a form directly absorbable through the mouth without need of assimilation through the digestive system.

Thirdly, it would be desirable to combine this formulation into carriers in common use, such as toothpaste, mouthwash, or chewing gum, so that individuals can gain the advantage of use without the need for taking a pill.

Fourthly, it would be desirable to combine this information into carriers commonly used in the environment of the dental office, carriers such as dental prophylaxis paste, oral subgingival irrigation fluid, or biologically absorbable or nonresorbable fiber matrices, so that the benefits of these key, orally absorbable nutrients, homeopathic remedies, and immune system stimulators can become part of the existing armamentarium of dentists and dental hygienists.

SUMMARY OF THE INVENTION

Generally speaking, in accordance with the invention, an orally absorbable improved dental formulation is provided. The dental formulation includes a base to which an active component is added. The active component includes one or more ingredients for physiologically and/or chemically reacting to the teeth or gums of a patient. Particularly, the active component comprises therein Vitamin C in an amount between about 0 and 25 weight percent, and coenzyme Q-10 (or ubiquinone) in an amount between 0 and 25 weight percent.

Optionally, Vitamin E may be added to the active component of the inventive composition in an amount in the active component between about 0 and 25 weight percent. Other ingredients that can be added to the active component include Vitamin A, the plant-based substance propolis, echinacea, and one or more homeopathic tissue salts.

In a preferred form, the inventive dental composition consists of a toothpaste composition, which when used, boosts the user's immune response to gum disease and tooth decay in addition to cleaning the teeth and freshening the breath. Although a toothpaste composition is preferred, the inventive formulation may be used in conjunction with a mouthwash or chewing gum. It may be also used in conjunction with dental treatment carriers such as prophylaxis paste and irrigation fluids.

In an alternative embodiment, the active component will include ubiquinone, but no Vitamin C, the ubiquinone will be present in an amount therein of between 0 and 25 weight percent. Other ingredients, as discussed above, may be added to the active component.

Accordingly, it is an object of the invention to provide an improved oral dental composition for enhancing the user's immune response to gum disease and tooth decay.

Yet another object of the invention is to provide a dental composition which is edible and safe.

Yet a further object of the invention is to provide a nutritionally active dental composition.

Still another object of the invention is to provide a biologically absorbable dental composition.

Still other objects and advantages of the invention will in part be obvious, and will in part be apparent from the following description.

The invention accordingly comprises the compositions embodying the features and construction, combination of elements and component parts as exemplified in the detailed disclosure hereinafter set forth, and the scope of the invention will be indicated in the claims.

DETAILED DESCRIPTION OF THE PREFERRED EMBODIMENTS

The inventive dental formulation, exclusive of the base to which it is added, includes, based on the overall weight of the active component, Vitamin C, and any precursor or derivative form thereof, in an amount between 0 and 25 weight percent and coenzyme Q-10 known as ubiquinone, in an amount also between about 0 to 25 weight percent. The Vitamin C component is in the form of either sodium ascorbate and/or calcium ascorbate, both of which are pH neutral, slightly abrasive, yet easily aborable forms of Vitamin C. Vitamin C is used in the inventive dental formulation in order to promote healing of the mouth from gum disease, and to reduce plaque build-up on the teeth. Coenzyme Q-10 is added to the inventive dental formulation for its known benefit in enhancing the health of the gums.

In addition to the Vitamin C and ubiquinone ingredients, the active component of the dental formulation of the invention may also include Vitamin E in an amount between about 0 and 25 weight percent, also based on the weight of the active component. Preferably, the Vitamin E ingredient is added to the formulation in the form of d-alpha tocopherol, which may also contain in addition or instead d-beta, d-gamma and d-delta tocopherols. This form of Vitamin E is may also be alpha tocopherols and/or Vitamin E esters. The Vitamin E ingredient is added to the inventive formulation because of its recognized value in promoting the healing of gum tissue.

Other ingredients which may be added to the active component of the inventive formulation include Vitamin A, propolis, echinacea, and one or more homeopathic tissue salts. If Vitamin A is added, it is added in an amount between 0 and 25 weight percent basis on the total weight of the active component. Vitamin A is preferably added in the form of water dispersed Vitamin A acetate, which is a dry fish oil free form of Vitamin A having the appearance of a beige powder. Vitamin A is added to the inventive formulation for its recognized value in the promotion of gum tissue healing.

Propolis is added to the active component of the inventive formulation in an amount between about 5 and 15 weight percent. Propolis is a plant-based substance used by bees in the construction of germ-free hives, and consists of a pale yellow powder. Propolis is added to the inventive formulation since it is well known to facilitate the fight against bacterial infections, for its stimulation of phagocytosis, for its use as a salve on abraded, bruised or inflamed mucous membranes, and otherwise for its overall stimulation of the immune system.

Echinacea is added to the active component of the inventive formulation in an amount between about 3 and 10 weight percent. Echinacea is an herbal extract of the Purple Cone Flower, and consists of a light brown liquid in a water/glycerin or water/10–20% alcohol vehicle. Echinacea is added to the dental formulation for its recognized properties in boosting the immune system so that the body is resistant to bacteria and viruses. Echinacea is also effective in reducing inflammation and stimulating lymphatic tissue drainage.

Grape seed extracts and other anti-oxidants, methyl sulfonyl methane, pycnogenol, and refined or unrefined cocoa, may also be added at levels of about 0% to 25% of the active component.

As discussed above, one or more homeopathic tissue salts may be included in the active component of the inventive formulation. The salts are added to the active component in an amount between 5 and 25 weight percent.

In a preferred formulation, the homeopathic tissue salt ingredient will consist of a complex of twelve homeopathic remedies, known collectively as the tissue salts. These consist of the following homeopathic tissue salts, each of which is in a potency in the range of between about 3 X and 15 X, and existing in an 80% water/20% alcohol medium.

Calc Fluor—used for its activity in reducing caries susceptibility and improving tissue elasticity.

Calc Phos—used for its activity in harmonizing bone and dental enamel metabolism.

Calc Sulph—used for its activity in purifying the blood and the tissues of the mouth, and for its role in improving the odor of the breath.

Ferr Phos—used for its action in mitigating inflammation and boosting the oxygen carrying capacity of the blood.

Kali Mur—used for its activity in aiding the general healing response.

Kali Phos—used for its activity for improving gum tissue health.

Kali Sulph—used for its activity in improving cellular metabolism and cell detoxification.

Mag Phos—used for its activity as a general tissue tonic.

Nat Mur—used for improved salivary gland activity.

Nat Phos—used as an acid neutralizer and as an aid to nutrient absorption.

Nat Sulph—used to improve gum tissue tone and to aid cells in purging intracellular toxins.

Silica—used in elimination toxins from tissues and improving tissue tone.

Alternatively, the homeopathic tissue formulation will be a four salt form comprising calc fluor, calc phos, calc sulph and silica.

In an alternative form, the active component of the inventive formulation will include ubiquinone in an amount in the active component of from 0–25 weight percent. The Vitamin C ingredient need not be added, but other active component ingredients can be added.

In addition to the active component of the inventive dental formulation, an optional component may also be added to and mixed with the active component base. The optional component will consist of at least one of cranberry extract, stevia, tangerine oil, and lemon oil.

The cranberry extract of the optional component would be present therein in an amount between about 20 and 50 weight percent. Cranberry extract is a red liquid of the Viburnum Oplus berry and is used in the formulation for its ability to prevent the adherence of bacteria to various structures of the mouth, as well as for its use as a flavoring agent. Cranberry extract may be bought from most conventional health food stores in either the form of encapsulated powder of the extract or in a liquid form.

Stevia may be added to the optional component formulation in an amount therein between about 25 and 50 weight percent. Stevia is an herbal extract of the Stevia Rebaudiana plant, and comprises a clear, slightly syrupy liquid. Stevia is used in the inventive formulation for its natural sweetness, while at the same time inhibiting the formation of plaque on teeth. It also serves the purpose of balancing the salty taste that is associated with the addition of sodium ascorbate (Vitamin C). Further, stevia reduces the craving for other plaque—and caries—producing sweets.

Tangerine oil may be part of the optional component in an amount between about 10 and 25 weight percent. Tangerine oil is the essential oil of the common fruit of the same name, and is merely added as a natural flavoring agent.

Lemon oil may also be added in an amount between about 10 and 25 weight percent to the optional component, and like the tangerine oil ingredient, it is the essential oil of the common fruit of the same name. It is used in the composition as a natural flavoring agent.

For a toothpaste, the base component of inventive formulation will include water in an amount between about 5 and 20 weight percent and glycerine in an amount between about 10 and 40 weight percent. The base preferably also includes abrasives such as calcium carbonate in an amount between about 20 and 40 weight percent and silica in an amount between about 20 and 40 weight percent. The water component can either be filtered, distilled or deionized. The glycerine component would preferably be vegetable glycerin, which is the sweet syrupy trihydroxy alcohol ($C_3H_8O_3$) derived from the manufacture of vegetable soap. It is added to the base both as a moisturizer and lubricant of the mouth, as well as to facilitate the cleansing of the teeth and the absorption of nutrients. It further functions as a liquid vehicle for forming the ingredients into an appropriate consistency.

The calcium component comprises an edible powder thereof. The silica component comprises an edible powder made by milling the mineral quartz. It is used in the base of the inventive formulation as a mild abrasive and consistency modulator.

Overall, the inventive formulation as a toothpaste will include an active component amount between about 8 and 33 weight percent, and a base component in an amount between 65 and 90 weight percent. If one or more of the ingredients of the optional component is added, optional component will be present in the overall toothpaste formulation in an amount between about 0.5 and 5 weight percent.

The most preferred toothpaste formulation in weight percent is as follows:

EXAMPLE 1

| | |
|---|---|
| Calcium Carbonate | 32% |
| Silica | 26% |
| Glycerine | 23% |
| Deionized water | 9% |
| Vitamin A | 2% |
| Vitamin C | 2% |
| Vitamin E | 2% |
| Co-enzyme Q-10 | 1% |
| Propolis | 0.6% |
| Echinacea | 0.4% |
| Homeopathics | 1% |
| Cranberry Ext. | 0.4% |
| Stevia Ext. | 0.3% |
| Tangerine oil | 0.17% |
| Lemon oil | 0.13% |

Other suitable formulations for toothpaste composition comprising both Vitamin C and ubiquinone are as follows:

EXAMPLE 2

| | |
|---|---|
| Calcium Carbonate | 32% |
| Silica | 26% |
| Glycerine | 23% |
| Deionized water | 9% |
| Vitamin C | 3.0% |
| Vitamin E | 3.7% |
| Co-enzyme Q-10 | 3% |
| Tangerine oil | 0.17% |
| Lemon oil | 0.13% |

EXAMPLE 3

| | |
|---|---|
| Calcium Carbonate | 32% |
| Silica | 26% |
| Glycerine | 23% |
| Deionized water | 9% |
| Vitamin A | 3% |
| Vitamin C | 3% |
| Co-enzyme Q-10 | 3% |
| Stevia Ext. | 1% |

EXAMPLE 4

| | |
|---|---|
| Calcium Carbonate | 32% |
| Silica | 26% |
| Glycerine | 23% |
| Deionized water | 8% |
| Vitamin C | 3% |
| Co-enzyme Q-10 | 3% |
| Propolis | 0.5% |
| Homeopathics | 2% |
| Cranberry Ext. | 2.5% |

EXAMPLE 5

| | |
|---|---|
| Calcium Carbonate | 32% |
| Silica | 26% |
| Glycerine | 23% |
| Deionized water | 9% |
| Vitamin C | 2.5% |
| Vitamin E | 3.5% |
| Co-enzyme Q-10 | 2.5% |
| Echinacea | 0.25% |
| Cranberry Ext. | 1.05% |
| Lemon oil | 0.2% |

EXAMPLE 6

| | |
|---|---|
| Calcium Carbonate | 32% |
| Silica | 26% |
| Glycerine | 23% |
| Deionized water | 9% |
| Vitamin A | 3.5% |
| Vitamin C | 2.5% |
| Co-enzyme Q-10 | 2.5% |
| Homeopathics (four salt form) | 0.5% |
| Stevia Ext. | 0.7% |
| Tangerine oil | 0.17% |
| Lemon oil | 0.13% |

Suitable formulations for the inventive toothpaste composition comprising just ubiquinone and other ingredients in the active component (other than Vitamin C) are as follows:

EXAMPLE 7

| | |
|---|---|
| Calcium Carbonate | 32% |
| Silica | 26% |
| Glycerine | 23% |
| Deionized water | 9% |
| Vitamin E | 4% |
| Co-enzyme Q-10 | 4% |
| Echinacea | 0.2% |
| Homeopathics (four salt form) | 0.5% |
| Cranberry Ext. | 1.1% |
| Tangerine oil | 0.2% |

EXAMPLE 8

| | |
|---|---|
| Calcium Carbonate | 32% |
| Silica | 26% |
| Glycerine | 23% |
| Deionized water | 9% |
| Vitamin A | 4% |

-continued

| | |
|---|---|
| Co-enzyme Q-10 | 3.5% |
| Propolis | 0.5% |
| Homeopathics | 1% |
| Cranberry Ext. | 0.75% |
| Stevia Ext. | 0.25% |

The inventive formulation may also be in the form of a dental prophylaxis paste. In this form, the base component comprises water in an amount between about 5 and 25 weight percent and glycerin in an amount between about 10 and 50 weight percent. It may also include calcium carbonate in an amount between about 20 and 40 weight percent, and silica in an amount between about 20 and 40 weight percent.

Overall, the inventive formulation as a prophylaxis paste will comprise between about 10 and 50 weight percent of the active component, and 48 to 88 weight percent of the base component. The optional component may be added in an amount between about 0.5 and 2 weight percent.

The most preferred prophylaxis paste composition in percent by weight is as follows:

EXAMPLE 9

| | |
|---|---|
| Calcium Carbonate | 29% |
| Silica | 25% |
| Glycerine | 9% |
| Deionized water | 9% |
| Vitamin A | 5.5% |
| Vitamin C | 5.5% |
| Vitamin E | 5.5% |
| Co-enzyme Q-10 | 5.5% |
| Propolis | 2% |
| Echinacea | 2% |
| Homeopathics | 1% |
| Cranberry Ext. | 0.4% |
| Stevia Ext. | 0.3% |
| Tangerine oil | 0.17% |
| Lemon oil | 0.13% |

Other suitable formulation for prophylaxis paste composition comprising both Vitamin C and ubiquinone are as follows:

EXAMPLE 10

| | |
|---|---|
| Calcium Carbonate | 29% |
| Silica | 25% |
| Glycerine | 9% |
| Deionized water | 9% |
| Vitamin A | 2% |
| Vitamin C | 8% |
| Vitamin E | 7.5% |
| Co-enzyme Q-10 | 10% |
| Tangerine oil | 0.3% |
| Lemon oil | 0.2% |

EXAMPLE 11

| | |
|---|---|
| Calcium Carbonate | 29% |
| Silica | 25% |

-continued

| | |
|---|---|
| Glycerine | 9% |
| Deionized water | 9% |
| Vitamin C | 8% |
| Vitamin E | 6.5% |
| Co-enzyme Q-10 | 10% |
| Echinacea | 0.5% |
| Cranberry Ext. | 2.8% |
| Lemon oil | 0.2% |

EXAMPLE 12

| | |
|---|---|
| Calcium Carbonate | 29% |
| Silica | 25% |
| Glycerine | 9% |
| Deionized water | 9% |
| Vitamin A | 8.5% |
| Vitamin C | 8% |
| Co-enzyme Q-10 | 10% |
| Homeopathics (four salt form) | 0.5% |
| Stevia Ext. | 0.7% |
| Tangerine oil | 0.17% |
| Lemon oil | 0.13% |

One possible formulation for a prophylaxis paste composition comprising just ubiquinone and other ingredients in the active component (other than Vitamin C) is as follows:

EXAMPLE 13

| | |
|---|---|
| Calcium Carbonate | 27% |
| Silica | 23% |
| Glycerine | 10% |
| Deionized water | 12% |
| Vitamin E | 13% |
| Co-enzyme Q-10 | 13% |
| Echinacea | 0.5% |
| Homeopathics (four salt form) | 0.5% |
| Cranberry Ext. | 0.8% |
| Tangerine oil | 0.2% |

In order to prepare the inventive formulation, the required amounts of Vitamin A powder, Vitamin C powder, Vitamin E powder, Propolis, and Co-enzyme Q-10 are first combined and milled together to yield a uniformly textured fine powder, which is the sum of the dry ingredients of the formulation.

Separately, the required amount of glycerine, water-, homeopathic tissue salts, Echinacea extract, Cranberry extract, Stevia extract, Tangerine oil, and Lemon oil are combined and thoroughly mixed. Essential oils such as lemon and tangerine oil may be use as solubilizers for the non-water soluble components of the active ingredient blend.

The dry ingredients of the formulation are then slowly added to the liquid ingredients while mixing, until a homogeneous slurry is produced.

Other possible delivery systems for the inventive formulation herein include toothpaste, prophylaxis paste or gel, coated dental floss, coated interproximal dental brush, mouthwash, resorbable membrane for application to gums and oral mucosa, chewing gum, lozenge, topically applied gel—either tray or directly to the gums and teeth, for use by patient and/or dental professional, topically applied solution, coated toothbrush, candy-gum drops, chocolate pieces or bars, nougats, etc., probably sugar free and non-cariogenic and nutritional supplements either for topical application or for ingestion.

To this slurry, the required amount of the milled calcium carbonate and silica powder is added incrementally while stirring until all of this powder has been incorporated, resulting in a homogenous mass of a suitable, paste-like composition for use as, on the one hand, the p composition of the invention, or, on the other hand, the dental prophylaxis paste composition of the invention.

In still a further form, the inventive formulation will include a base and at least one of cranberry extract in an amount between about 0.1 and 5 weight percent and stevia (a specific herbal extract) in an amount between about 0.1 and 4 weight percent, the weight percents based on the overall weight of the formulation. One or more active component ingredients, as discussed hereinabove, may be added to this alternative formulation.

Examples of this additional embodiment as a toothpaste composition are as follows:

EXAMPLE 14

| | |
|---|---|
| Calcium Carbonate | 35% |
| Silica | 31% |
| Glycerine | 26% |
| Deionized water | 6% |
| Cranberry Ext. | 1.8% |
| Lemon oil | 0.2% |

EXAMPLE 15

| | |
|---|---|
| Calcium Carbonate | 35% |
| Silica | 32% |
| Glycerine | 16.5% |
| Deionized water | 5% |
| Propolis | 1% |
| Echinacea | 0.4% |
| Homeopathics | 0.5% |
| Stevia Ext. | 0.6% |

Examples of this additional embodiment as a prophylaxis paste composition are as follows:

EXAMPLE 16

| | |
|---|---|
| Calcium Carbonate | 35% |
| Silica | 32% |
| Glycerine | 16.5% |
| Deionized water | 14.5% |
| Cranberry Ext. | 1.8% |
| Lemon oil | 0.2% |

EXAMPLE 17

| | |
|---|---|
| Calcium Carbonate | 36% |
| Silica | 31% |
| Glycerine | 15.5% |

| | |
|---|---|
| Deionized water | 13.5% |
| Propolis | 1.0% |
| Echinacea | 1.0% |
| Homeopathics | 1.0% |
| Stevia Ext. | 1.0% |

It will thus be seen that the objects set forth above, among those made apparent from the preceding description, are efficiently attained, and since certain changes may be made in the above compositions, without departing from the spirit and scope of the invention, it is intended that all matter contained in the above description shall be interpreted as illustrative, and not in a limiting sense.

It is also to be understood that the following claims are intended to all of the generic and specific features of the invention herein described, and all statements of the scope of the invention, which, as a matter of language, might be said to fall there between.

What is claimed is:

1. An orally absorbable dental formulation comprising a base and an active component, wherein the active component includes Vitamin C in an amount not more than 25 weight percent, and ubiquinone in an amount not more than 25 weight percent, the weight percents based on the total weight of the active component, provided that when the amount of Vitamin C is 0%, the amount of ubiquinone is greater than 0% and when the amount of ubiquinone is 0%, the amount of Vitamin C is greater than 0%.

2. The formulation of claim 1, further comprising Vitamin B in an amount not more than 25 weight percent, Vitamin A in an amount not more than 25 weight percent, propolis in an amount between about 5 and 15 weight percent, echinacea in an amount between about 3 and 10 weight percent, grape seed extracts in an amount of not more than 25 weight percent, and one or more homeopathic tissue salts in an amount between about 5 and 25 weight percent, the weight percent based on the overall weight of the active component.

3. The formulation of claim 1, wherein said base component is present in the formulation in an amount between about 65 and 90 weight percent, and said active component is present in the formulation in an amount between about 8 and 33 weight percent, the weight percent based on the overall weight of the formulation, and the formulation forms a toothpaste.

4. The formulation of claim 1, wherein said base component is present in the formulation in an amount between about 48 and 88 weight percent, and said active component is present in the formulation in an amount between about 10 and 50 weight percent, the weight percent based on the overall weight of the formulation, and the formulation forms a prophylaxis paste.

5. The formulation of claim 3, wherein said base component comprises at least one of water in an amount between about 5 and 25 weight percent, glycerine in an amount between about 10 and 50 weight percent, calcium carbonate in an amount between about 20 and 40 weight percent, and silica in an amount between about 20 and 40 weight percent, the weight percents based on the overall weight of the base component.

6. The formulation of claim 1, further including an optional component comprising at least of one cranberry extract, stevia, tangerine oil and lemon oil.

7. The formulation of claim 2, wherein the homeopathic tissue salt is selected from the group consisting of Calcium Fluoride, Calcium Phosphate, Calcium Sulphate, Iron Phosphate, Potassium Chloride, Potassium Phosphate, Potassium Sulphate, Magnesium Phosphate, Sodium Chloride, Sodium Phosphate, Sodium Sulphate and Silica.

8. The formulation of claim 2, wherein the homeopathic tissue salt has potency in the range of between about 3× and 15×.

9. The formulation of claim 2, wherein the homeopathic tissue salt exists in 80% water/20% alcohol medium.

10. The formulation of claim 1, which comprises a mouthwash.

11. The formulation of claim 1, which comprises chewing gum.

12. The formulation of claim 1, which comprises a subgingival irrigation fluid.

13. The formulation of claim 1, which comprises coated fiber.

14. The formulation of claim 13, wherein said coated fiber is floss.

15. The formulation of claim 13, wherein said coated fiber is toothbrush bristle.

16. The formulation of claim 1, which comprises interproximal dental brush.

17. The formulation of claim 1, which comprises lozenge.

18. The formulation of claim 1, which comprises topically applied solution.

19. The formulation of claim 1, which comprises candy-gum drops.

20. The formulation of claim 1, which comprises chocolate pieces, bars or nougats.

21. A method of boosting immune response to gum diseases or tooth decay comprising administering the formulation of claim 1 to a patient by absorption through the mouth.

22. A method of reducing gingival bleeding comprising administering the formulation of claim 1 to a patient by absorption through the mouth.

23. A method of reducing periodontal attachment loss comprising administering the formulation of claim 1 to a patient by absorption through the mouth.

24. A method of increasing collagen density in gingival comprising administering the formulation of claim 1 to a patient by absorption through the mouth.

25. A method of reducing inflammation in gingival sulcus comprising administering the formulation of claim 1 to a patient by absorption through the mouth.

26. A method of reducing plaque formation comprising administering the formulation of claim 1 to a patient by absorption through the mouth.

27. A method of reducing plaque adhesion to teeth or tonque comprising administering the formulation of claim 1 to a patient by absorption through the mouth.

28. A method of reducing permeability of bacterial toxins to epithelial cell wall comprising administering the formulation of claim 1 to a patient by absorption through the mouth.

29. A method of reducing collagenase enzyme activity in the presence of bacteria comprising administering the formulation of claim 1 to a patient by absorption through the mouth.

30. A method of increasing cellular respiration and oxygen saturation of cells comprising administering the formulation of claim 1 to a patient by absorption through the mouth utilizing a periodontal attachment apparatus.

31. A method of reducing the incidence of apthus ulcers on oral mucosa comprising administering the formulation of claim 1 to a patient by absorption through the mouth.

32. A method of reducing the duration of apthus ulcers in mouth comprising administering the formulation of claim 1 to a patient by absorption through the mouth.

33. A method of reducing bad breath comprising administering the formulation of claim 1 to a patient by absorption through the mouth.

34. A method of cleaning teeth comprising administering the formulation of claim 1 to a patient by absorption through the mouth.

35. A method of removing surface staining from teeth comprising administering the formulation of claim 1 to a patient by absorption through the mouth.

36. A method of whitening teeth comprising administering the formulation of claim 1 to a patient by absorption through the mouth.

37. A method of enhancing dental health of humans and animals by topically administering the formulation of claim 1.

38. A method of treating or preventing gum diseases and tooth decay of humans and animals by topically administering the formulation of claim 1.

39. A composition for an orally absorbable dental formulation comprising a base and the active component composition comprising Vitamin C in an amount between about 0 and 25 weight percent and ubiquinone in an amount between about 0 and 25 weight percent, the weight percent based on the overall weight of the active component.

40. The composition of claim 1, further including at least one of Vitamin E in an amount not more than 25 weight percent, Vitamin A in an amount not more than 25 weight percent, propolis in an amount between about 5 and 15 weight percent, echinacea in an amount between about 3 and 10 weight percent, grape seed extracts in an amount of not more than 25 weight percent, and one or more homeopathic tissue salts in an amount between about 5 and 25 weight percent, the weight percent based on the overall weight of the active component.

\* \* \* \* \*